United States Patent [19]

Bloomquist

[11] Patent Number: 4,690,673

[45] Date of Patent: * Sep. 1, 1987

[54] DUAL MODE I.V. INFUSION DEVICE WITH DISTAL SENSOR

[75] Inventor: Ted C. Bloomquist, San Diego, Calif.

[73] Assignee: IMED Corporation, San Diego, Calif.

[ * ] Notice: The portion of the term of this patent subsequent to Oct. 14, 2003 has been disclaimed.

[21] Appl. No.: 844,414

[22] Filed: Mar. 26, 1986

Related U.S. Application Data

[63] Continuation-in-part of Ser. No. 801,987, Nov. 26, 1985, Pat. No. 4,617,014.

[51] Int. Cl.⁴ .......................................... A61M 31/00
[52] U.S. Cl. .................................... 604/67; 604/131; 604/246; 128/DIG. 12; 128/DIG. 13
[58] Field of Search ..................... 604/67, 131, 246; 128/DIG. 12, DIG. 13

[56] References Cited

U.S. PATENT DOCUMENTS

| | | | |
|---|---|---|---|
| 2,420,148 | 5/1947 | Ostergren | 277/351 |
| 2,770,703 | 11/1956 | Scheurich | 201/63 |
| 2,885,520 | 5/1959 | Giovanni | 201/63 |
| 3,218,864 | 11/1965 | Schugt | 73/407 |
| 3,505,634 | 4/1970 | Von Vick | 338/4 |
| 3,778,195 | 12/1973 | Bamberg | 417/474 |
| 3,866,473 | 2/1975 | Teitelbaum et al. | 73/398 AR |
| 4,306,460 | 12/1981 | Sakurai et al. | 73/721 |
| 4,309,908 | 1/1982 | Rapp et al. | 73/720 |
| 4,345,476 | 8/1982 | Singh | 73/720 |
| 4,346,705 | 8/1982 | Pekkarinen et al. | 128/214 F |
| 4,373,525 | 2/1983 | Kobayashi | 128/124 E |
| 4,468,219 | 8/1984 | George et al. | 604/66 |
| 4,479,797 | 10/1984 | Kobayashi et al. | 604/153 |
| 4,526,574 | 7/1985 | Pekkarinen | 604/52 |
| 4,617,014 | 10/1986 | Cannon et al. | 604/67 |

Primary Examiner—C. Fred Rosenbaum
Assistant Examiner—John D. Ferros
Attorney, Agent, or Firm—Workman, Nydegger & Jensen

[57] ABSTRACT

An improved dual mode peristaltic device is provided for infusing I.V. solutions to a patient through an I.V. tube. In a first mode of operation, the device functions as a peristaltic pump and in the second mode of operation it functions like a controller. Included in the device and associated with the I.V. tube is a pressure sensing strain gauge assembly that monitors dimensional changes in the outer diameter of the I.V. tube as an indication of fluid pressure changes in the tube. The strain gauge assembly is positioned relative to the device's peristaltic means to alternately monitor fluid pressure in a patent I.V. tube upstream and downstream from the gauge assembly. A pair of stationary fingers surround the strain gauge assembly to isolate it from the pulsitile nature of the peristaltic action of the device. In the first mode (pump mode), the device is programmed to alarm and cease operation when fluid pressure downstream from the gauge assembly reaches a preselected value. In the second mode (controller mode), the device is programmed to alarm and cease operation when there is no differential between fluid pressure upstream and downstream from the gauge assembly.

20 Claims, 11 Drawing Figures

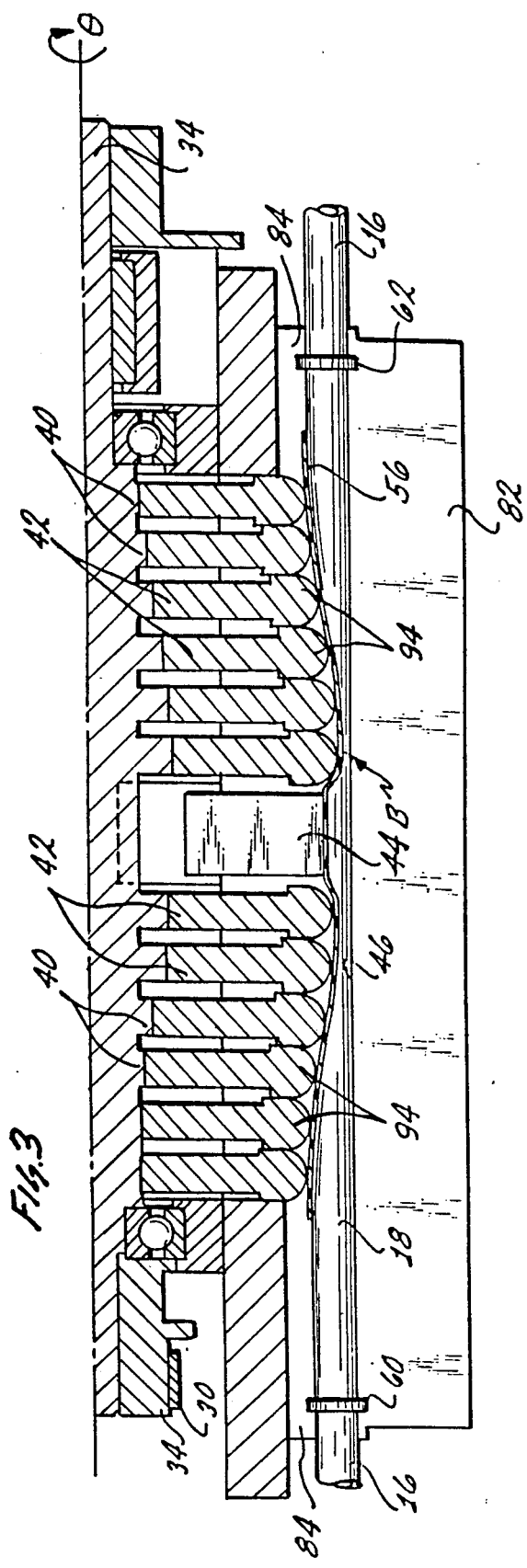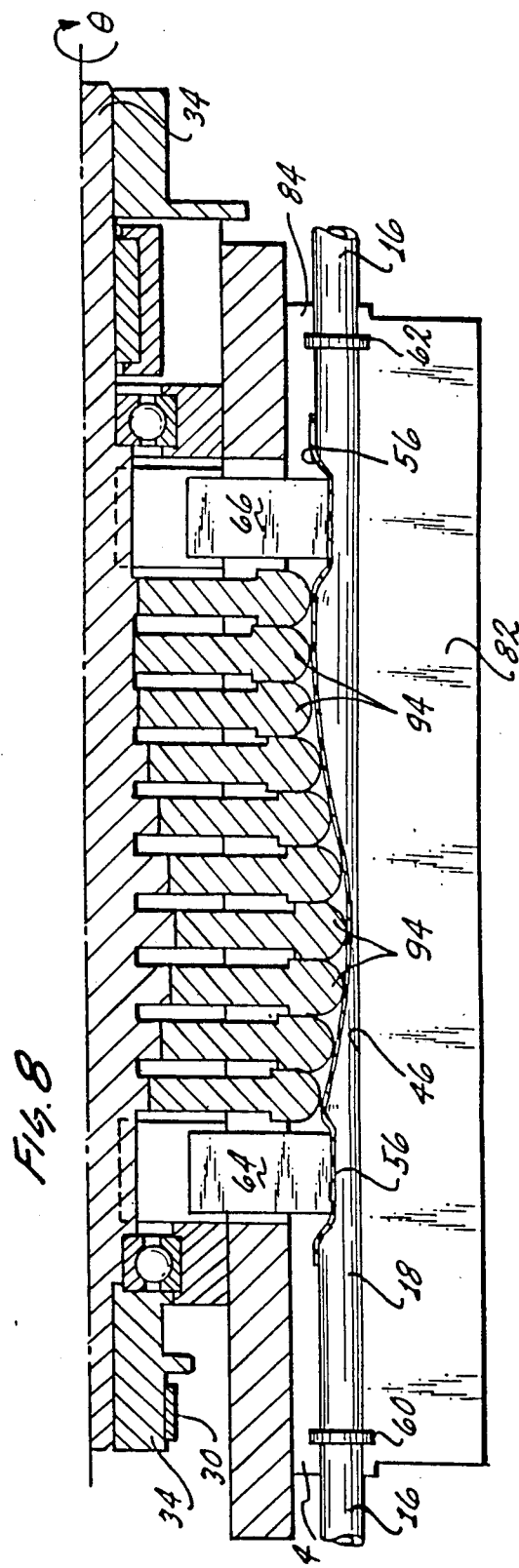

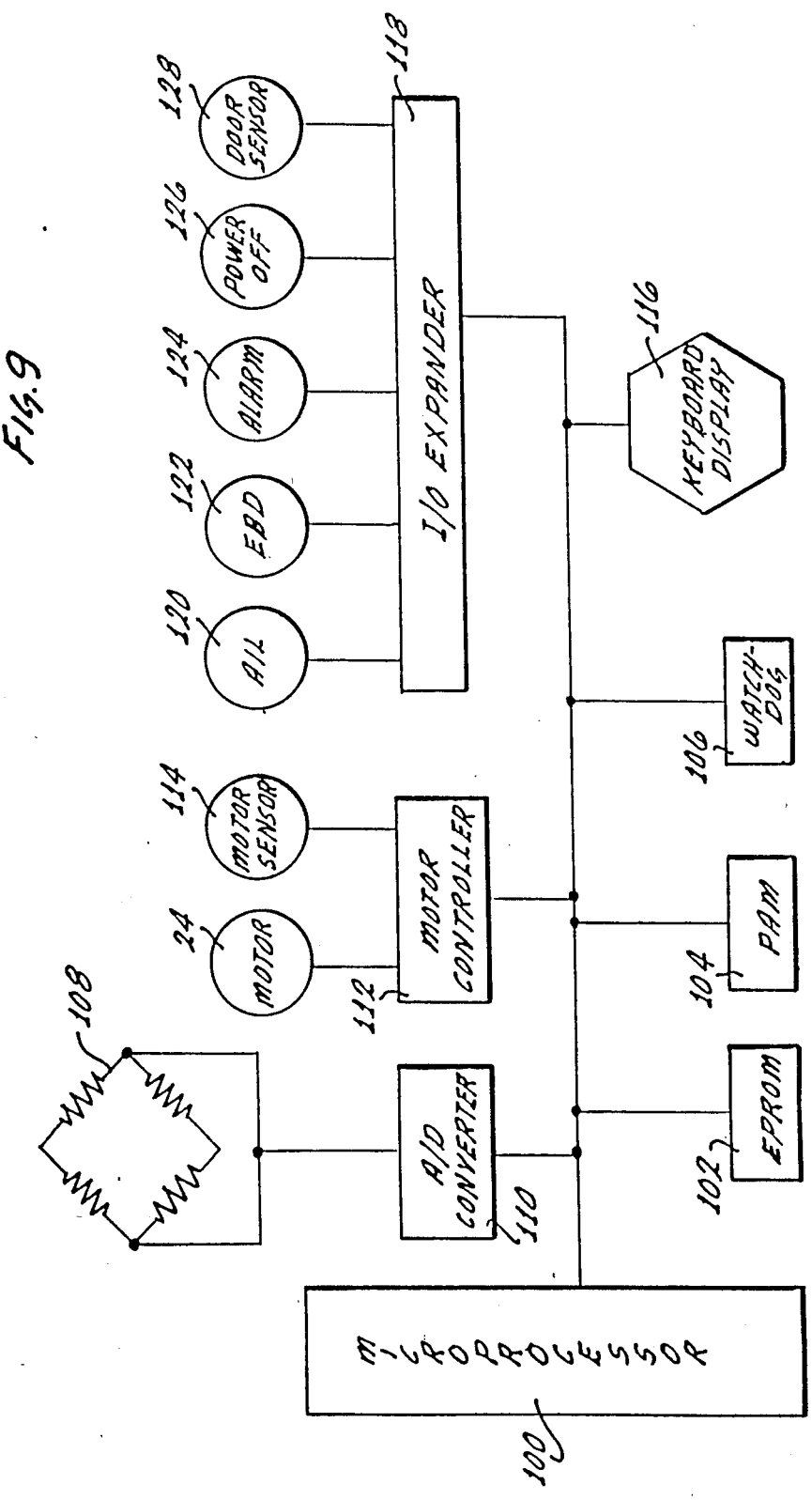

DUAL MODE I.V. INFUSION DEVICE WITH DISTAL SENSOR

BACKGROUND OF THE INVENTION

This application is a continuation-in-part of my prior application for a "Dual Mode I.V. Infusion Device," Ser. No. 801,987 filed Nov. 26, 1985 now U.S. Pat. No. 4,617,014 issued Oct. 14, 1986. This invention relates generally to a device used for the infusion of medical solutions to a patient. More specifically, the present invention relates to a dual mode device which can alternately function either as an infusion pump or as a controller. This invention is particularly though not exclusively, useful for the intranveous infusion of medical solutions to a patient under conditions where the flexibility of a dual mode capability is desired.

DESCRIPTION OF THE PRIOR ART

Many medical devices have been proposed to infuse medical solutions to a patient. Indeed, in recent years the use of such devices has gained wide acceptance. Consequently, a variety of medical solution infusion devices have been suggested for use in numerous medical and surgical applications. Typically, these devices can be grouped into either of two categories. The first group is generically referred to as controllers and the second group is referred to as pumps. Examples of medical devices in each category are so numerous it is not deemed instructive to list them here.

It is instructive, however, to understand the basic difference between a pump and a controller. Fundamentally, controllers are medical devices which connect with a gravity feed I.V. administration line for the purpose of controlling the rate of fluid flow through the line. In I.V. administration systems where controllers are used, the fluid pressure for delivering fluid to the patient is dependent solely on the system head height. In other words, fluid pressure in the system depends on the bottle height of the fluid source above the patient. In such a system, the function of the controller is to constrict the tubing of the administration set to regulate the rate of fluid flow through the tubing. The controller does not contribute to the fluid pressure.

Several advantages are obtained by using controllers. Firstly, as mentioned above, they provide a means for controlling the rate of fluid flow through a gravity system. Secondly, controllers are generally perceived by hospital personnel as being safe since they operate at low fluid pressures and thus are not apt to cause tissue damage to the patient at the injection site. Further, they are easily understood and rather simple to use. An example of a controller which is widely used throughout the medical profession at the present time is disclosed in U.S. Pat. No. 4,300,552 to Cannon which is assigned to the same assignee as the present invention.

Unlike controllers, medical devices in the second group, i.e. pumps, provide a mechanical action on fluid within the system to establish an artificial fluid for the system. The medical devices properly grouped into this category are of several types and include, but are not necessarily limited to, cassette-type pumps, syringe pumps, diaphragm pumps and peristaltic pumps. As should be expected, the use of pumps for the infusion of medical solutions provides certain advantages which are not attainable by a controller. Importantly, these advantages may be very necessary in a particular medical application. For example, an I.V. pump is better suited than is a controller to (a) overcome resistance to fluid flow caused by small gauge catheters and small gauge I.V. tubing; (b) infuse the more viscous fluids; (c) overcome in vivo resistance; (d) achieve higher fluid flow rates; and (e) provide perceptively a higher degree of volumetric accuracy. These advantages are due, in large part, to the fact that pumps exert a mechanical pressure on the fluid prior to the infusion of the fluid into the patient whereas controllers depend on gravity to move fluid through the system. An example of an I.V. pump is disclosed in U.S. Pat. No. 3,985,133 to Jenkins which is assigned to the same assignee as the present invention.

Regardless of the type of I.V. infusion system used, it is widely recognized that the ability to monitor fluid pressure in the fluid line is a distinct advantage for the safe operation of any I.V. administration system. Specifically, but regardless whether it be a pump or a controller, where electro-mechanical medical devices are employed and fluid pressure within the line can be determined, the medical device can be programmed to react to changes in the fluid pressure. For example, in a pumping system, if the detected fluid pressure of the line rises above some predetermined level, an occlusion in the system may be indicated and it would be advantageous to have the medical device cease operation. Likewise, with a controller, if the detected fluid pressure rises above a predetermined level, an occlusion may be indicated and the infusion should be stopped.

The importance of knowing the fluid pressure in an I.V. administration system is underscored by the fact that several proposals have been made for devices which monitor physical characteristics of the fluid flow line and correlate changes in these characteristics to changes in fluid pressure. In one such system, as disclosed in U.S. Pat. No. 4,526,574 to Pekkarinen, a differential occlusion sensing apparatus is disclosed which monitors the location of a portion of the I.V. tube and translates variations of the location measurement from a base location into a fluid pressure indication. In another system, as disclosed in U.S. Pat. No. Re. 31,315 to Jenkins et al. and assigned to same assignee as for the present invention, the fluctuations of a diaphragm in fluid communication with the fluid flow are monitored as being indicative of the fluid pressure level.

It will be appreciated that in a hospital environment, circumstances can dictate whether there is a need for a pump or a controller. Presently, depending on the situation, hospital personnel must obtain a pump for situations wherein a pump is required and obtain a controller for those situations requiring a controller. Not only does this require the availability of two separate medical devices, it also requires knowledge and skills for their separate set up and operation. Until the present invention, there has been no single unitary medical device capable of obtaining the desired advantage of either a pump or a controller.

In light of the above, the present invention recognizes the separate and distinct advantages obtainable by using pumps or controllers and the benefits to be derived in I.V. administration systems which have fluid pressure monitoring capabilities. Specifically, the present invention recognizes the desirability of obtaining the combined advantages of a pump and a controller from a single universal device which, depending on the desires of the operator, can function either as an I.V. pump or like a controller and which thereby obtains the desired advantage of the particular mode of operation. In accordance with the present invention, this dual mode capability is made possible by providing the system with a fluid pressure sensor which permits modal operation in compliance with detectable pressure limitations. Also, with electronic controls to cease operation of the system whenever elevated fluid pressure indicates an occlusion, the dual mode medical device of the present invention can be safely operated regardless of its selected mode of operation. Specifically, where a peristaltic pump is used, this invention recognizes that the necessary fluid pressure information for a dual mode device can be obtained by alternately monitoring fluid pressure in the patent I.V. tube upstream and downstream from the moving zone of occlusion.

Accordingly, one object of the present invention is to provide a single medical device which can be switched to function either as a peristaltic pump or like a controller. Another object of the present invention is to provide a dual mode device which is directly operable on an I.V. tube for the infusion of medical solutions to a patient and is thus non-invasive of the fluid line. It is still another object of the present invention to provide a cost effective, relatively accurate and easy to use medical device for the infusion of medical solutions to a patient.

SUMMARY OF THE INVENTION

The preferred embodiment of the present invention comprises a medical device for infusing I.V. fluids to a patient through an I.V. tube in which the device is operatively engageable with a portion of the I.V. tube. Upon engagement of the device with the I.V. tube, a peristaltic means in the device is positioned against a portion of the I.V. tube to sequentially squeeze the I.V. tube and produce a moving zone of occlusion along the tube for pumping fluid therethrough in accordance with the peristaltic action. The device further includes a strain gauge assembly which is positioned against the I.V. tube and operatively associated with the peristaltic pumping means so as to be able to monitor fluid pressure downstream and upstream of the occlusion respectively before and after the occlusion has passed the point at which the gauge assembly is operatively associated with the I.V. tube. For the improved embodiment of the present invention, the strain gauge assembly is located near the distal end of the peristaltic means to maximize the time the gauge monitors fluid pressure downstream from the occlusion. The improved embodiment also includes a pair of stationary fingers with one finger disposed upstream and adjacent to the strain gauge assembly and the other finger disposed downstream and adjacent to the strain gauge assembly to isolate the strain gauge assembly from the action of the peristaltic means. The present invention further includes means to switch the device between one mode of operation wherein the strain gauge assembly monitors only the fluid pressure downstream from the occlusion (the pumping mode) and another mode wherein the strain gauge assembly is able to alternately monitor the fluid pressure in the I.V. line upstream and downstream from the occlusion (the controller mode).

In the first or pumping mode, the device of the present invention is provided with microprocessor programmed means to alarm and cease operation of the pump whenever the strain gauge assembly indicates that fluid pressure downstream from the occlusion has reached a preselected value. In the controller mode of operation, the device is microprocessor programmed to alarm and/or cease operation when the differential between fluid pressure downstream from the peristaltic occlusion and the fluid pressure upstream from the peristaltic occlusion is a null.

The novel features of this invention, as well as the invention itself, will be best understood from the accompanying drawings, taken together with the accompanying description, in which similar reference characters refer to similar parts and in which:

BRIEF DESCRIPTION OF THE DRAWINGS

FIG. 3 is a portion of the peristaltic assembly as shown in FIG. 2 with the peristaltic action taking place at a different location;

FIG. 8 is a cross-sectional view of a portion of a peristaltic assembly of an alternate embodiment of the present invention;

FIG. 9 is a block diagram of the electronic components of the present invention;

DESCRIPTION OF THE PREFERRED EMBODIMENT

Figure 1:
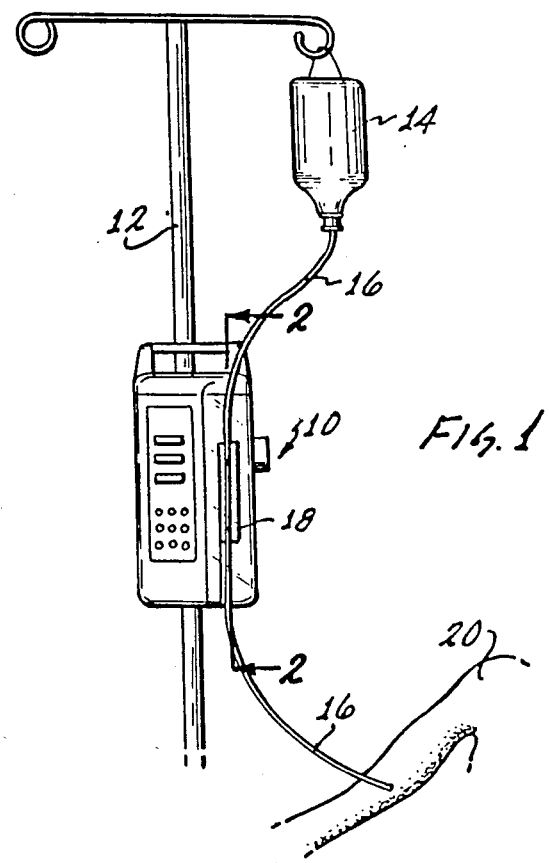
FIG. 1 shows the device in its environment for infusing medical solutions from a fluid source to a patient.

Referring initially to FIG. 1, a controller/pump generally designated 10 is shown in its intended environment. The controller/pump 10 is mounted on I.V. pole 12 in a manner well known in the art. An I.V. fluid source 14 is hung from the I.V. pole 12 as shown in FIG. 1, and an I.V. tube 16 is connected in fluid communication with fluid source 14 and operatively connected with controller/pump 10 in a manner as generally shown in FIG. 1. Downstream from its point of engagement with controller/pump 10, I.V. tube 16 is coupled with patient 20 for the infusion of medical solutions to the patient 20.

Figure 2:
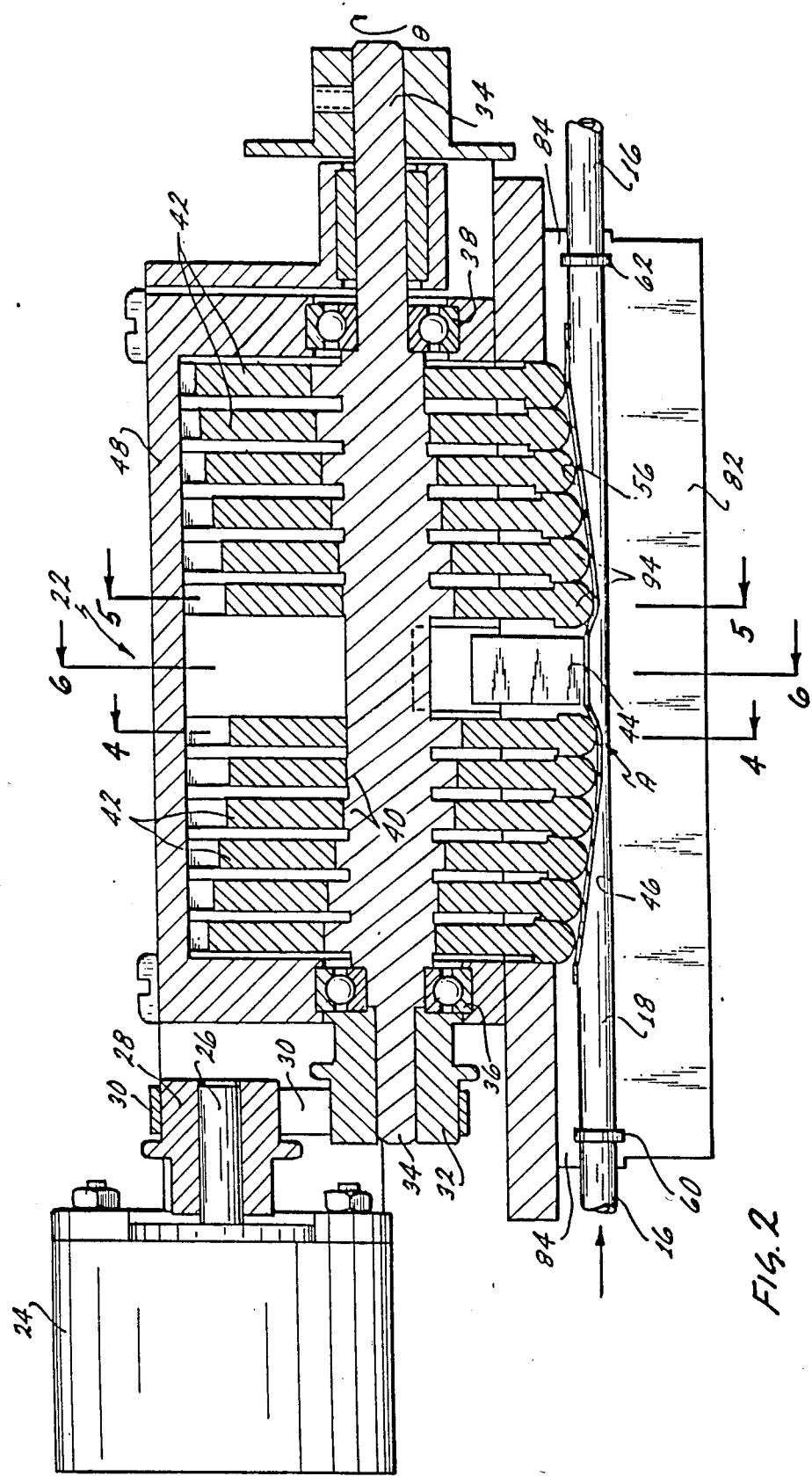
FIG. 2 is a cross-sectional view of the peristaltic assembly as seen along the line 2—2 in FIG. 1 and rotated into the position as shown for clarity.

FIG. 2 is a cross-sectional view of the peristaltic assembly, generally designated 22, which is shown here in isolation from controller/pump 10 for purposes of clarity. As shown in FIG. 2, peristaltic assembly 22 includes a motor 24 which is preferably a stepper motor but may be of any type well known in the relevant art. A drive shaft 26 is rotated by the stepper motor 24 and is secured to an attachment 28 by any means well known in the art in a manner which permits the rotation of attachment 28 to move a drive pulley 30. Drive pulley 30 is connected in operative engagement with an attachment 32 that is in turn secured to cam shaft 34 by any means well known in the art. The cam shaft 34 is supported on peristaltic assembly 22 by a bushing 36 and a bushing 38. Fixed on cam shaft 34 at predetermined locations along the axis of the cam shaft 34 is a series of cam lobes 40. As will be appreciated by those skilled in the pertinent art, cam lobes 40 are eccentrically mounted on cam shaft 34 in a helical pattern along the axis of cam shaft 34 in a manner which will create a peristaltic action by the movement of the fingers 42. The movement of the individual fingers 42 will be best appreciated by reference to FIG. 4.

Figure 4:
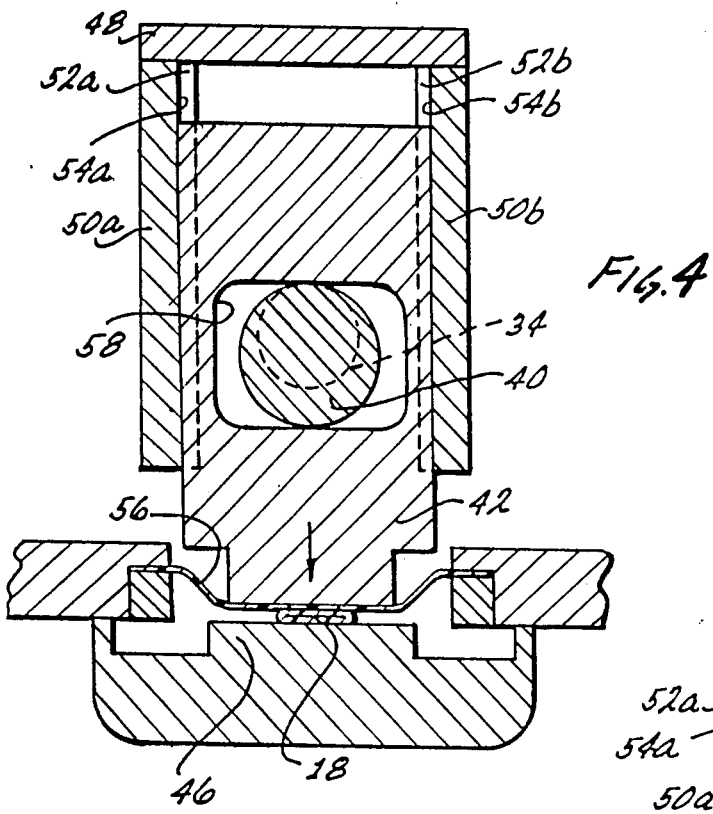
FIG. 4 is a cross-sectional view of a portion of the peristaltic assembly as seen along the line 4—4 in FIG. 2.
Figure 5:
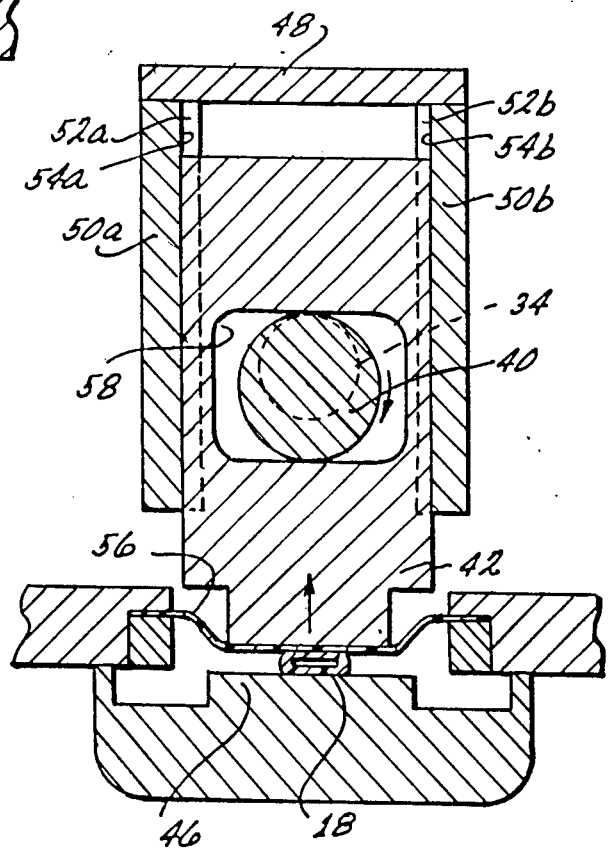
FIG. 5 is a cross-sectional view of a portion of the peristaltic assembly as seen along the line 5—5 in FIG. 2.

Referring to FIG. 4, it is seen that each of the individual fingers 42 are formed with an aperture 58 to receive an individual cam lobe 40 therein. Each finger 42 is mounted in housing 48 of the peristaltic assembly 22 in a manner which provides for movement of the finger 42 in a direction substantially perpendicular to the longitudinal axis of cam shaft 34. It will be appreciated with reference to FIG. 4 that the housing 48 comprises a side 50a and a side 50b which are formed with baffles 52a and 52b to create gooves 54a and 54b that maintain the alignment of finger 42 relative to cam shaft 34. A cross-reference of FIG. 4 with FIG. 5 shows that the rotation of cam shaft 34 causes a consequent rotation of the eccentrically mounted cam lobe 40 which, in turn, urges against respective portions of the aperture 58 to cause a reciprocal vertical motion of finger 42 within the housing 48. Referring back to FIG. 2 or FIG. 3, it can be appreciated by the skilled artisan that cam lobes 40 can be sequentially located along cam shaft 34 in a helical manner. With cam lobes 40 so located, rotation of cam shaft 34 causes fingers 42 to move in a direction substantially perpendicular to the axis of cam shaft 34 and in a manner which will provide a peristaltic action by the concerted movement of the various fingers 42.

Again referring to FIG. 2, it will be seen that the I.V. tube 16 can be placed in operative contact with the peristaltic assembly 22 by location of the respective fitments 60 and 62 into the base 84 of peristaltic assembly 22. As shown in FIG. 2, a pumping section 18 of I.V. tube 16 can be defined between fitments 60 and 62. This particular pumping section 18 may be made of the same material as I.V. tube 16. However, in the preferred embodiment, the pumping section 18 comprises a very flexible and compressible elastomeric material. Such elastomer may be a silicone rubber of the type identified as RX 50 and manufactured by Dow Corning. It will also be appreciated by reference to FIG. 2 or FIG. 3 that once I.V. tube 16 and its associated pumping section 18 have been mounted on peristaltic assembly 22, a door 82 can be closed to provide a platen 46 that is positioned against pumping section 18, as shown, and which provides resistance against the motion of the fingers 42 as they urge on pumping section 18. Also shown in FIG. 2 and FIG. 3, a membrane 56 is located between the ends 94 of fingers 42 and pumping section 18 to separate fingers 42 from pumping section 18 and provide for the isolation of I.V. tube 16 and pumping section 18 from the peristaltic assembly 22. Again, it will be appreciated by the skilled artisan that depending upon cam shaft rotation θ and the helical orientation of cam lobes 40 along cam shaft 34, a particular finger 42 can be caused to urge against pumping section 18. Further, it will be appreciated that each complete revolution of cam shaft 34 causes a sequential progression of the fingers 42 to urge against pumping section 18 and generate a peristaltic action against pumping section 18.

The specific action of fingers 42 on pumping section 18 is best seen by cross-referencing FIG. 4 and FIG. 5. These figures respectively show the action of a finger 42 that causes an occlusion on pumping section 18 and a patentcy condition on pumping section 18. It will be appreciated by the skilled artisan that a moving zone of occlusion is created as cam shaft 34 is rotated to cause a sequential urging of fingers 42 against pumping section 18.

Figure 10:
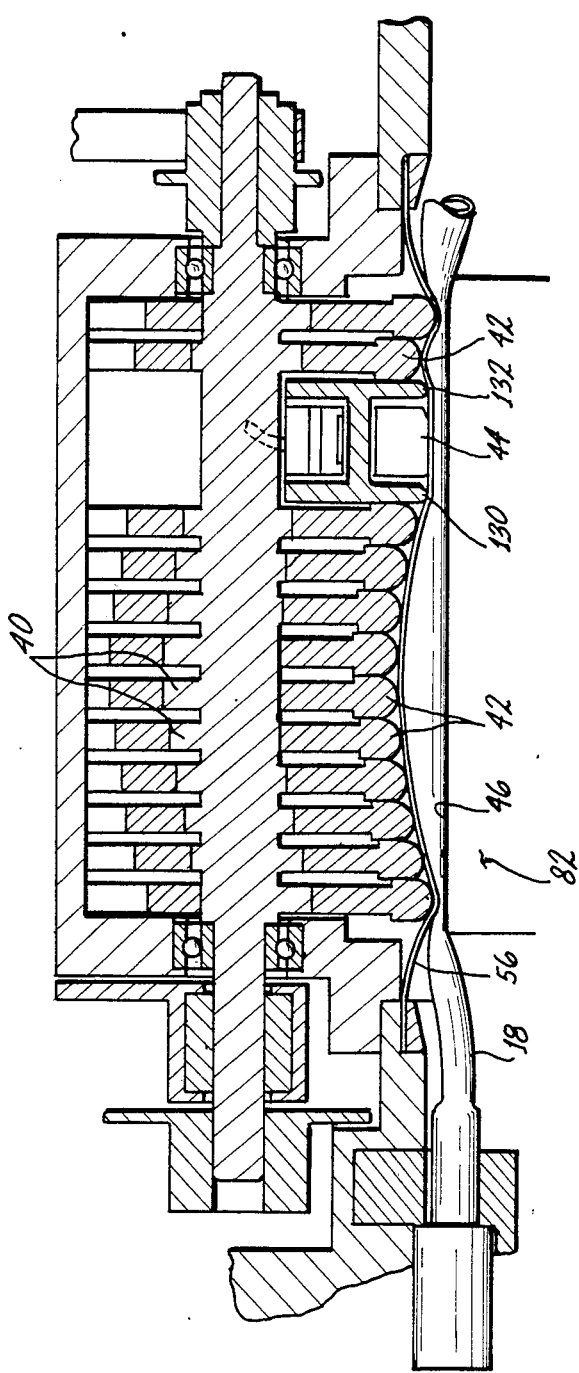
FIG. 10 is a cross-sectional view of a portion of the peristaltic assembly of the improved embodiment of the present invention.

The preferred embodiment of the present invention also includes a gauge assembly 44 which is associated with peristaltic assembly 22 and mounted with respect to the fingers 42 of peristaltic assembly 22 as generally shown in FIG. 2 and FIG. 3. An improved embodiment of the present invention associates the gauge assembly 44 with peristaltic assembly 44 near the distal or downstream end of the peristaltic assembly 44 as generally shown in FIG. 10. A more detailed description of the gauge assembly 44 can be obtained with reference to FIG. 6.

Figure 6:
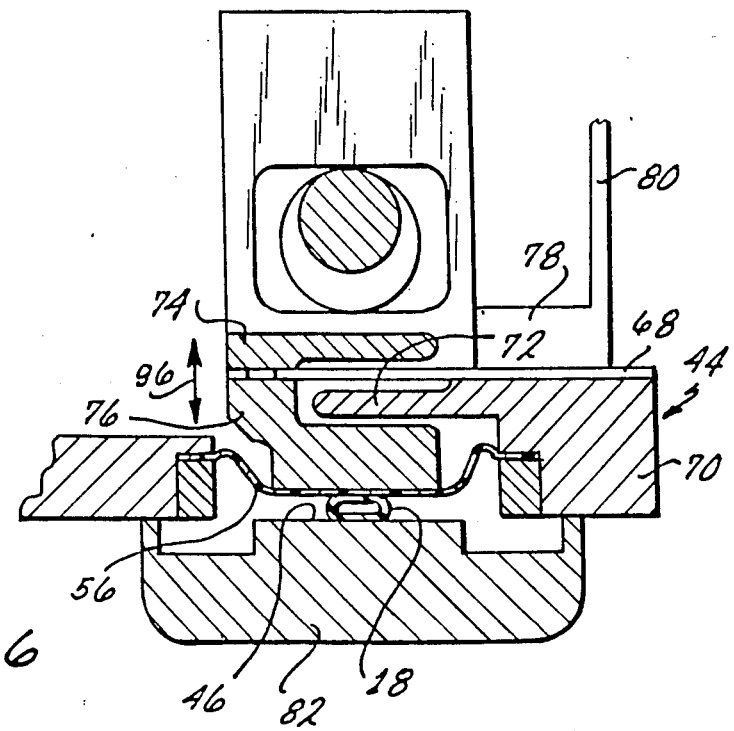
FIG. 6 is a cross-sectional view of the strain gauge assembly of the peristaltic assembly as seen along the line 6—6 in FIG. 2.

In FIG. 6 the gauge assembly 44 is shown in cross-section and is seen to include a mounting block 70 on which is fixedly mounted a cantilevered strain beam 68. On the surface of cantilevered strain beam 68, but not shown in FIG. 6, is a strain gauge. The entire assembly which comprises block 70, strain beam 68 and strain gauge 108 is of a type similar to model No. X1680 manufactured by Transducers, Inc., 14030 Bolsa Lane, Cerritos, Calif. 90701. Extending from mounting block 70, as shown in FIG. 6, is a travel limiter 72. Mounted on the opposite side of the cantilevered strain beam 68 opposite from the travel limiter 72 is a protective extension 74. Fixedly attached to cantilevered strain beam 68 at the end opposite from its connection with mounting block 70 is a pressure transmitting member 76 which is positioned to physically connect the end of cantilevered strain beam 68 with pumping section 18 upon engagement of the I.V. tube 16 with the controller/pump 10. Also connected with cantilevered strain beam 68 is an electrical junction block 78 that provides a connection for the electrical circuitry from the strain gauge (not shown). Electrical wiring 80 provides further connection between the cantilevered strain beam 68 and the electronic components of the present invention for a purpose to be subsequently discussed.

As will be appreciated by reference to FIG. 6, upon engagement of I.V. tube 16 with controller/pump 10, a portion of pumping section 18 is positioned between platen 46 of door 82 and the pressure transmitting member 76 which is directly and physically connected with the cantilevered strain beam 68. As also seen in FIG. 6 and previously discussed, a membrane 56 can be placed between the pressure transmitting member 76 and pumping section 18 for the purposes of isolating the peristaltic mechanism from the functional I.V. administration set being used in conjunction with the controller/pump 10 and protecting the interior of controller/pump 10 from tampering and contaminants.

Referring now to FIG. 9, the electronic componentry of the controller/pump 10 is set forth in block diagram form. As seen in FIG. 9, this componentry includes a microprocessor 100 which may be of any type well known in the pertinent art. For example, a microprocessor as manufactured by Intel Corporation, model No. 8032, can be used for the purposes of the present invention. Electrically connected to microprocessor 100 is an EPROM 102 which provides code information for the operation of microprocessor 100. Also electrically connected to microprocessor 100 is a RAM 104 which has the capacity to store and preserve various system parameters during a power condition. It will be appreciated by the skilled artisan that EPROM 102 and RAM 104 are of types well known in the pertinent art. Examples of these components which will satisfy the requirements of the present invention are respectively a model No. D27512 manufactured by Intel and a model No. HM6116 manufactured by Hitachi. Also electrically connected to microprocessor 100 is a watchdog circuit 106 which provides for system integrity. More specifically, watchdog circuitry 106 insures that stepper motor 24 and microprocessor 100 are functioning correctly. Additionally, watchdog circuit 106 provides a reset capability for the system and provides means for stopping the operation of the system.

Also shown in FIG. 9 is a strain gauge 108. It will be recalled that strain gauge 108 was not shown in the earlier description of gauge assembly 44. As can now be more easily appreciated, it is the strain gauge 108 which is electrically attached to cantilevered strain beam 68. With this attachment the flexures of cantilevered strain beam 68 which are caused by the movement of pressure transmitting member 76 in response to variations in the outer diameter of pumping section 18 will be sensed by the strain gauge 108. Electronically, it can be appreciated that the analog voltage measurements obtained from strain gauge 108 represent a voltage which requires conversion by an A/D converter 110 before it is electrically compatible with microprocessor 100. As shown in FIG. 9, the ciruitry for this electrical connection is provided.

Also shown in FIG. 9 is the electrical relationship of the stepper motor 24 with microprocessor 100. As seen in FIG. 9, it is necessary for stepper motor 24 to be directly connected with motor controller 112. A motor sensor 114 (also generally known as a shaft encoder) is also directly connected with motor controller 112 and generates electronic signals which correlate the running of motor controller 112 with the position of cam shaft 34 as indicated by cam shaft rotational position $\theta$. A keyboard/display 116 is provided to permit operator access to the electronic componentry of the controller/pump 10. Through keyboard/display 116 an operator is able to key in the various system parameters which are necessary to operate the controller/pump 10. It is through keyboard/display 116 that an operator selects the mode of operation for controller/pump 10 and establishes the preselected values for fluid pressure limitations in the selected mode of operation. Together with input from keyboard/display 116, microprocessor 100 operates in accordance with code from EPROM 102 and input from RAM 104. One result obtained from this arrangement is that a reading on strain gauge 108 can be read by microprocessor 100 in accordance with a preset program.

As envisioned in the present invention, motor sensor 114 monitors cam shaft position $\theta$. Based on cam shaft position $\theta$, input from motor sensor 114, motor controller 112 provides signals to microprocessor 100 which are compared and timed according to a prepared program. Microprocessor 100 also receives signals from A/D converter 110 which have been generated by strain gauge 108 in response to movements of cantilevered strain beam assembly 68. Recall that readings from strain gauge assembly 64 are correlated to fluid pressure readings in I.V. tube 16. Microprocessor 100 is preprogrammed to accept fluid pressure readings from strain gauge 108 at selected times which depend on cam shaft position $\theta$ as indicated by motor sensor 114. Further, microprocessor 100 is preprogrammed to compare the fluid pressure readings from strain gauge 108 with the modal fluid pressure limitations established by the operator. Stepper motor 24 is then run in accordance with programmed signals from microprocessor 100 to operate the structure of controller/pump 10 as discussed elsewhere in this disclosure.

Further in FIG. 9, it is shown that various peripheral electrical components may be added to the controller/pump 10 to expand its capabilities. Examples of peripheral equipment that could be included within a system for controller/pump 10 is shown in FIG. 9 and connections between these peripheral componentry and microprocessor 100 is accomplished by way of an I/O expander 118. As seen in FIG. 9, an air-in-line detector (AIL) 120, an empty bottle detector (EBD) 122 and a door sensor 128 are examples of peripheral equipment which could be incorporated into the controller/pump 10 system. Also shown in FIG. 9 and electrically connected to I/O expander 118 is an alarm 124 and a power off switch 126. In all respects the electronic componentry of the present invention are made from electronic elements which are well known in the pertinent art and are commercially available. It will be understood and appreciated that the electronic componentry system as set forth in FIG. 9 is merely illustrative and that its purpose is to provide a background which is electronically compatible with the structural integrity and the cooperation of structure of the controller/pump 10 of the present invention FIG. 8 shows an alternate embodiment of the present invention which employs two gauge assemblies as opposed to the single gauge assembly 44 disclosed for the preferred embodiment. In the alternate embodiment, a gauge assembly 64 is positioned at the upstream end of the peristaltic fingers 42 and a second gauge assembly 66 is positioned at the downstream end of the peristaltic fingers 42. In all respects, gauge assemblies 64 and 66 are similar in structure to that as disclosed for gauge assembly 44 and incorporate all of the elements previously described for gauge assembly 44. It will be understood that electronic componentry for the alternate embodiment need not include provision for alternately reading gauge assemblies 64 and 66. Instead, continuous readings may be taken and used in a logic sequence similar to that for the preferred embodiment.

FIG. 10 shows an improved embodiment of the present invention in which a single gauge assembly 44 is located near the distal or downstream end of the peristaltic assembly. This location accomplishes two purposes. First, with gauge assembly 44 near the distal end of peristaltic assembly 22, gauge assembly 44 acts as a sensor which remains downstream from the occlusion during a greater portion of the cycle of rotation $\theta$ for cam shaft 34. Thus, gauge assembly 44 monitors or senses the more critical fluid pressure in the IV line between the occlusion and the patient for a longer period of time. Second, this positioning causes gauge assembly 44 to not monitor downstream pressure at a time when there is only low incremental flow downstream from controller/pump 10 to the patient. Thus, the distal positioning of gauge assembly 44 minimizes both the time and the amount of unmonitored pressurized fluid flow to the patient from controller/pump 10.

The improved embodiment also includes stationary fingers 130 and 132 which are adjacent gauge assembly 44 and respectively located upstream and downstream from gauge assembly 44. As best seen in FIG. 10, stationary fingers 130 and 132 urge against pumping section 18 but do not cause an occlusion of the section 18. Instead, fingers 130 and 132 remain a predetermined fixed distance from platen 46 to allow fluid flow through section 18 while isolating gauge assembly 44 from the effects of the peristaltic action of fingers 42. Stationary fingers 130 and 32 may be fixedly attached to peristaltic assembly 22 by any means well known in the art.

OPERATION

In its operation controller/pump 10 is placed in operative engagement with an I.V. tube 16. This is done by positioning I.V. tube 16 against base 84 of peristaltic assembly 22 as shown in FIG. 2. With tube 16 in this position, the fitments 60 and 62 are operatively engaged with base 84. As discussed previously, the portion of I.V. tube 16 that is placed against membrane 56 and in operative engagement with controller/pump 10 is preferably a flexible and compressible pumping section 18.

Once I.V. tube 16 with its pumping section 18 have been engaged with controller/pump 10, the door 82 is closed. The closure of door 82 causes platen 46 to come in contact with pumping section 18 and enclose pumping section 18 between platen and membrane 56.

Activation of stepper motor 24 causes rotation of drive shaft 26 in a manner that causes drive pulley 30 to rotate cam shaft 34. The actual positioning of cam shaft 34 is represented by cam shaft rotation $\theta$. As will be appreciated by those skilled in the art, a complete revolution of cam shaft 34 will cause cam lobes 40 to reciprocate fingers 42 substantially perpendicular to the axis of pumping section 18. Due to the helical configuration of cam lobes 40 on cam shaft 34, fingers 42 urge against pumping section 18 to create a moving zone of occlusion along the length of pumping section 18 during each revolution of cam shaft 34. For example, an occlusion, such as the one represented in FIG. 2 by the character A, is caused to move along the length of pumping section 18 and create a peristaltic pumping action.

During operation of the peristaltic assembly 22, it will be appreciated by reference to FIG. 6 that gauge assembly 44 can be positioned to determine dimensional differences in the outer diameter of pumping section 18. As seen in FIG. 6, pumping section 18 is located directly between platen 46 and membrane 56. During the pumping of fluid through pumping section 18, the outer diameter of pumping section 18 will vary, dependent upon the fluid pressure within pumping section 18. This variation in pressure will cause a consequent variation in the distance between membrane 56 and platen 46 on respectively opposite sides of the center portion of pumping section 18. It will be appreciated by those skilled in the pertinent art that this change in dimension can be correlated to changes in the fluid pressure within the pumping section 18. As will be further appreciated by those skilled in the art, a variation in the outer diameter of pumping section 18 and the consequent change in distance between membrane 56 and platen 46 will cause a motion of pressure transmitting member 76 generally in an up and down direction as indicated by the arrow 96. Further, it will be appreciated that the movement of pressure transmitting member 76 in a direction as indicated by arrow 96 will be manifested as a fluctuation of the cantilevered strain beam 68. With a strain gauge, or strain gauges, (not shown in FIG. 6) mounted on cantilevered strain beam 68, the fluctuations of cantilevered strain beam 68 can be electronically measured and transmitted to a microprocessor 100.

It should be recognized that the motion of pressure transmitting member 76 in the direction of arrow 96 is limited by the travel limiter 72. This is a safety feature for the controller/pump 10 since travel limiter 72 precludes a motion of pressure transmitting member 76 through a distance that could break or permanently bend the cantilevered strain beam 68. This safety feature is particularly important because it prevents any inadvertent manipulation of pressure transmitting member 76 that could damage cantilevered strain beam 68.

Figure 7:
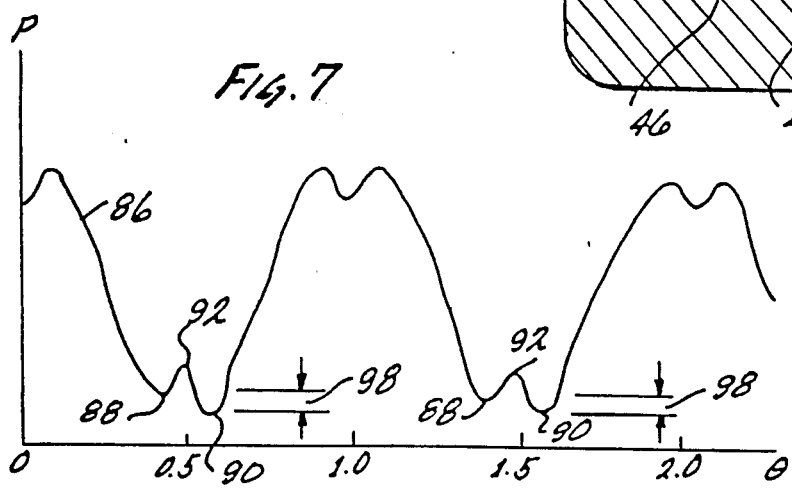
FIG. 7 is a graph showing periodic variation in fluid pressure as a function of the peristaltic action of the device.
Figure 11:
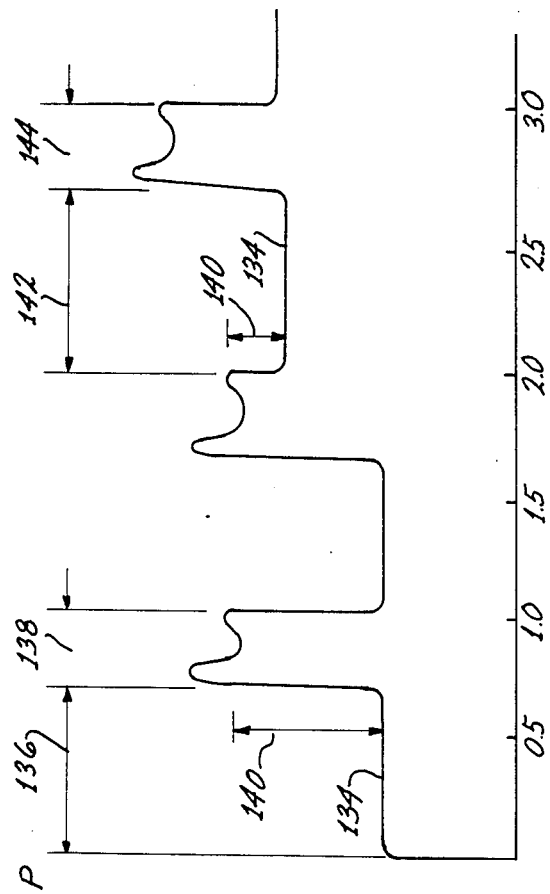
FIG. 11 is a graph showing periodic variation in fluid pressure as a function of the peristaltic action of the improved embodiment of the device.

As previously indicated, controller/pump 10 can be operated in either one of two modes. Operation in the controller simulation mode requires operation of the components in a manner as now described. It has been recognized that the fluid pressure in I.V. tube 16 will generally vary according to the periodic cycles of graph 86 as presented in FIG. 7. As seen in FIG. 7, the graph 86 depicts variations in fluid pressure P at a set point within I.V. tube 16 as a function of cam shaft rotation $\theta$. Stated differently, for successive revolutions of cam shaft 34, the variation in fluid pressure P at a particular point will vary in a manner depicted by the graph 86. It has been determined, however, that when gauge assembly 44 is isolated by stationary fingers 130 and 132 and moved to a distal position relative to peristaltic assembly 22 as substantially shown in FIG. 10, gauge assembly 44 will observe a periodic fluctuation of fluid pressure as generally depicted on the graph 134 in FIG. 11.

Referring back to the structure of controller/pump 10, it is seen that the peristaltic assembly 22 as shown in FIG. 2 has been activated to the point where cam shaft rotation $\theta$ causes a peristaltic finger 42 to occlude pumping section 18 at location A. It has been determined that during operation when peristaltic assembly 22 is in this configuration, the fluid pressure in the section of pumping section 18 contacting gauge assembly 44 corresponds to points 88 on graph 86 in FIG. 7. Further, when peristaltic assembly 22 has moved to cause an occlusion of pumping section 18 at point B, as shown in FIG. 3, the fluid pressure in the section of pumping section 18 contacting gauge assembly 44 corresponds with the points 90 on graph 86 in FIG. 7. The points 92 on graph 86 in FIG. 7 indicate the pressure in the portion of pumping section 18 in contact with gauge assembly 44 during the transition of the occlusion from point A, as shown in FIG. 2, to the point B, as shown in FIG. 3.

It will be further appreciated by those skilled in the relevant art that during normal operation of the controller/pump 10 in the simulated controller mode, the fluid pressure upstream from the occlusion caused by peristaltic assembly 22 will be dependent upon the height of fluid source 14. The downstream pressure during such operation, because of the occlusion created on pumping section 18 by peristaltic assembly 22, will be a value less than the upstream fluid pressure. Specifically, an upstream fluid pressure reading can be made by gauge assembly 44 when the occlusion is at point B as shown in FIG. 3, and a downstream fluid pressure reading can be made by gauge assembly 44 when the occlusion is at point A as shown in FIG. 2. Further, it has been found that the differential, indicated by the character 98 on graph 86 in FIG. 7, between the upstream pressure indicated at point 88 and the downstream pressure indicated at point 90 will be relatively constant during normal operation of controller/pump 10. Under these conditions, controller/pump 10 will be programmed to rotate cam shaft 34 at an angular velocity which will provide the fluid flow rate preselected by the operator.

Since fluid pressure in a controller is normally established by bottle height, i.e., the height of the fluid source 14 above the patient 20, controller/pump 10 needs to be sensitive to this parameter. Accordingly, for normal operation of controller/pump 10 in the simulated controller mode, any decrease in differential 98 would indicate that the upstream pressure (indicated by point 88) should also be increased to maintain a differential 98. This can be accomplished very simply by the operator raising fluid source 14 to increase the hydrostatic pressure in I.V. tube 16 upstream from the occlusion caused by peristaltic assembly 22. It is recognized, however, that there is a limit on the height to which an operator may be willing to raise the fluid source 14. Consequently, when fluid source 14 has been raised as high as the operator feels is safe and the differential 98 continues to diminish or reaches a null, an alarm condition should be dictated. Accordingly, when switched into the controller mode, controller/pump 10 should be programmed through appropriate circuitry shown in FIG. 9 to alarm and cease operation where there is no longer a differential 98.

In all important functional respects, the improved embodiment of controller/pump 10, as shown in FIG. 10, operates in the same manner described above for the embodiment shown in FIGS. 2 and 3. The improved embodiment, however, provides a more uniform reading of the fluid pressure variations in the IV tube. This will be better appreciated by referring to FIG. 11 in which the fluid pressure variations in pumping section 18 at the location of gauge assembly 44 in the improved embodiment are shown for several rotations $\theta$ of cam shaft 34. As depicted by graph 134 in FIG. 11, the region 136 corresponds to that portion in the revolution of cam shaft rotation $\theta$ during which gauge assembly 44 monitors fluid pressure downstream from the occlusion (i.e., fluid pressure seen by the patient). As will be appreciated by the skilled artisan, this downstream pressure is generated by the peristaltic action of controller/pump 10. On the other hand, the region 138 corresponds to that portion in the revolution of cam shaft rotation $\theta$ during which gauge assembly 44 monitors fluid pressure upstream from the occlusion (i.e., fluid pressure due to the height of fluid source 14 above the occlusion). This pressure is frequently referred to as "bottle height." FIG. 11 also shows subsequent cycles of cam shaft revolutions and similar corresponding regions when gauge assembly 44 is monitoring upstream and downstream pressure.

Insofar as the operation of controller/pump 10 in the controller mode is concerned, it is the difference between the upstream and downstream fluid pressures that is important. Normally, the upstream fluid pressure (region 138) must be greater than the downstream fluid pressure (region 136). This relationship insures that the patient is not subjected to any greater pressure than would be caused by only "bottle height." Differential 140 may, however, vary somewhat without affecting operation. For example, if the downstream pressure increases only slightly, such as evidenced by the change seen when comparing region 142 with region 136, there may be no cause for concern. Such a pressure increase may be due to some inconsequential crimping of I.V. tube 16 or change inpatient position. To overcome such a situation, the operator can raise fluid source 14 and thereby increase the upstream pressure. The result of raising fluid source 14 is to change upstream pressure to a level as shown in region 144. Of course, there is a limit on "bottle height." Thus, whenever differential 140 remains a null, despite attempts to maintain an actual differential 140 by raising fluid source 14 to increase "bottle height," a potentially dangerous situation for the patient is indicated and controller/pump 10 will cease operation in a manner as previously discussed.

It is appreciated that the present invention need not necessarily be limited to the medical field for use in infusing medical solutions to patients. Indeed, a controller/pump according to the present invention may be useful in any application wherein pressurized flow of fluids at relatively low flow rates is desired.

When controller/pump 10 is to be used in the pumping mode, the upstream fluid pressure in I.V. tube 16 becomes of much less importance. In this mode of operation, cam shaft 34 is caused to rotate with an angular velocity which will provide a peristaltic action by peristaltic assembly 22 in a manner that provides the desired rate of fluid flow. The crucial consideration in this mode of operation will be the downstream fluid pressure in I.V. tube 16 which may increase to a level that indicates an occlusion downstream from controller/pump 10. Thus, by having the electronic components of controller/pump 10 monitor the downstream pressure in I.V. tube 16, a condition can be detected wherein the downstream pressure exceeds some preselected maximum. Such a preselected maximum can be established that either indicates a possible occlusion or an otherwise harmful condition for the patent 20. Thus, when controller/pump 10 is operating in the pumping mode, the downstream pressure in I.V. tube 16 is monitored and upon reaching a preselected maximum, electronic circuitry is programmed to alarm controller/pump 10 and cease its operation.

While the particular controller/pump as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

I claim:

1. A device for pumping fluids from a fluid source through a tube having a compressible pumping section, which device comprises:

a case;

means for holding a portion of said compressible pumping section on said case;

peristaltic means mounted on said case and operatively engaged with said tube to sequentially squeeze said pumping section and produce at least one moving zone of occlusion along said pumping section for infusing fluids to the patient;

a gauge fixedly mounted on said case and operatively coupled with said pumping section, at a predetermined location thereon, for sensing fluid pressure in said pumping section at said location at a first time when said I.V. tube downstream from said location is patent and at a second time when said I.V. tube upstream from said location is patent;

a first stationary finger disposed upstream from and adjacent to said gauge;

a second stationary finger disposed downstream from and adjacent to said gauge;

means to determine a pressure differential between said first time and said second time; and means to alarm and cease operation of said device when said pressure differential attains a predetermined value.

2. A device as cited in claim 1 wherein said peristaltic means is a linear peristaltic pump having an upstream end and a downstream end.

3. A device as cited in claim 2 wherein said pumping section is made of an elastomeric material.

4. A device as cited in claim 3 wherein said gauge is a strain gauge associated with said peristaltic means and positioned to engage said pumping section intermediate said upstream end and said downstream end of said peristaltic means.

5. A device as cited in claim 4 wherein said gauge is positioned near the downstream end of said peristaltic means.

6. A device as cited in claim 5 further comprising means to selectively cause said device to alarm and cease operation when the differential attains a predetermined minimum value.

7. A device as cited in claim 5 further comprising:

means for selectively disregarding the fluid pressure in said pumping section at said second time; and means to alarm and cease operation of said device when the fluid pressure at said first time attains a predetermined value.

8. A device for infusing medical solutions to a patient which comprises:

a fluid source;

a compressible tube connecting said fluid source in fluid communication with the patient;

a case having means for engagingly receiving a portion of said tube therein;

means mounted on said case and engageable with said portion of said tube for generating a moving zone of occlusion thereon to pump fluid from said source to the patient;

a gauge mounted on said case and operatively associated with said tube to alternately measure the outside diameter of said tube at a first time when said tube downstream from said gauge is patent and at a second time when said tube upstream from said gauge is patent;

a first stationary finger disposed upstream from and adjacent to said gauge;

a second stationary finger disposed downstream from and adjacent to said gauge;

means for comparing the measurement at the first time with the measurement at the second time to establish a differential; and means to alarm said device and cease operation when said differential attains a predetermined value.

9. A device as cited in claim 8 wherein said portion of said tube is made of an elastomeric material.

10. A device as cited in claim 9 wherein said gauge is synchronized with said pumping means to establish the first time when said zone of occlusion is upstream from said gauge and to establish the second time when said zone of occlusion is downstream from said gauge.

11. A device as cited in claim 10 wherein said gauge is a strain gauge.

12. A device as cited in claim 11 wherein said pumping means is a linear peristaltic pump having a first end and a second end, and said second end is positioned downstream from said first end.

13. A device as cited in claim 12 wherein said gauge is mounted on said pumping means near said second end.

14. A device as cited in claim 13 wherein said gauge is noninvasive of said tube.

15. A device as cited in claim 14 wherein said engaging means is formed having a peripheral portion that comprises a flexible membrane separating said tube from said pumping means.

16. A device as cited in claim 14 wherein said tube further comprises a first fitment and a second fitment to define said portion of said tube, and said case further comprises a first attaching means and a second attaching means respectively engageable with said first and second fitments to engageably receive said tube.

17. A device as cited in claim 15 further comprising means to selectively cause said device to alarm and cease operation when the differential has attained a predetermined minimum value.

18. A device as cited in claim 16 further comprising:

means for selectively disregarding the fluid pressure in said pumping section at said second time; and means to alarm and cease operation of said device when the fluid pressure at said first time attains a predetermined value.

19. A method for infusing I.V. medical fluids from a fluid source to a patient through an I.V. tube having a compressible pumping section which comprises the steps of:

A. Engaging said pumping section with a device comprising: a case; means for holding a portion of said compressible pumping section on said case; peristaltic means mounted on said case and operatively engaged with said tube to sequentially squeeze said pumping section and produce at least one moving zone of occlusion along said pumping section for infusing fluids to the patient;

B. Monitoring the fluid pressure at a fixed location of said pumping section with a gauge having a first stationary finger disposed upstream from and adjacent to said gauge and a second stationary finger disposed downstream from and adjacent to said gauge being operatively coupled with said pumping section for sensing fluid pressure in said pumping section at said location at a first time when said I.V. tube downstream from said location is patent and at a second time when said I.V. tube upstream from said location is patent;

C. Determining a pressure differential between said first time and said second time; and D. Discontinuing the infusion of fluids to the patient when said pressure differential attains a predetermined minimum value.

20. The method as cited in claim 19 further comprising the steps of:

E. selectively disregarding the monitoring of fluid pressure at said second time and the determination of said pressure differential; and F. discontinuing infusion of fluids to the patient when said fluid pressure at said first time attains a predetermined value.

* * * * *